United States Patent
Yang et al.

(10) Patent No.: US 12,110,282 B2
(45) Date of Patent: Oct. 8, 2024

(54) THIOBENZOPYRANS AND THEIR USE IN PREPARATION OF DRUGS FOR TREATMENT OF RHEUMATOID ARTHRITIS

(71) Applicant: HC SYNTHETIC PHARMACEUTICAL CO., LTD., Xi'an (CN)

(72) Inventors: Cheng Yang, Xi'an (CN); Dongxing Li, Xi'an (CN); Sumin Qi, Xi'an (CN); Qiyuan Zhang, Xi'an (CN); Xiaodan Zhao, Xi'an (CN)

(73) Assignee: HC SYNTHETIC PHARMACEUTICAL CO., LTD., Shaanxi (CN)

( * ) Notice: Subject to any disclaimer, the term of this patent is extended or adjusted under 35 U.S.C. 154(b) by 29 days.

(21) Appl. No.: 18/013,069

(22) PCT Filed: Jul. 22, 2021

(86) PCT No.: PCT/CN2021/107802
§ 371 (c)(1),
(2) Date: Dec. 27, 2022

(87) PCT Pub. No.: WO2022/022372
PCT Pub. Date: Feb. 3, 2022

(65) Prior Publication Data
US 2023/0242502 A1 Aug. 3, 2023

(30) Foreign Application Priority Data
Jul. 25, 2020 (CN) .................. 202010726564.9

(51) Int. Cl.
*C07D 335/06* (2006.01)
*A61P 19/02* (2006.01)

(52) U.S. Cl.
CPC ............ *C07D 335/06* (2013.01); *A61P 19/02* (2018.01)

(58) Field of Classification Search
CPC .................................................. C07D 335/06
See application file for complete search history.

(56) References Cited

U.S. PATENT DOCUMENTS 4,954,518 A  9/1990  Takano et al.

FOREIGN PATENT DOCUMENTS

| CN | 101597271 A | 12/2009 |
|----|-------------|---------|
| CN | 101597272 A | 12/2009 |
| JP | H0597840 A  | 4/1993  |

OTHER PUBLICATIONS

Inaba "Synthesis and Antiinflammatory Activity of 7-Methanesulfonylamino-6-phenoxychromones. Antiarthritic Effect of the 3-Formylamino Compound (T-614) in Chronic Inflammatory Disease Models" Chem. Pharm. Bull. 2000, 48(1) 131-139.*
Patani "Bioisosterism: A Rational Approach in Drug Design" Chemical Reviews 1996, 96, 3147-3176.*
Geissler "Benzopyranones and benzothiopyranones: A class of tyrosine protein kinase inhibitors with selectivity for the v-abl kinase." Cancer Research, 1992, 52(16), 4492-8.*
Nussbaumer "2-Substituted 4-(Thio)chromenone 6-O-Sulfamates: Potent Inhibitors of Human Steroid Sulfatase" Journal of Medicinal Chemistry, 2002, 45(19), 4310-4320.*
Tomaru "A Simple Decision Tree Suited for Identification of Early Oral Drug Candidates With Likely Pharmacokinetic Nonlinearity by Intestinal CYP3A Saturation" Journal of Pharmaceutical Sciences 110 (2021) 510-516.*
ISR for PCT/CN2021/107802, Sep. 13, 2021.
Wang et al. "Synthesis of Iguratimod", Chinese Journal of New drugs, vol. 15, No. 23, ( Dec. 31, 2006), pp. 2042-2044.

* cited by examiner

*Primary Examiner* — David K O'Dell
(74) *Attorney, Agent, or Firm* — AKC PATENTS, LLC; Aliki K. Collins (57) ABSTRACT

Provided is a thiobenzopyran-based compound of Formula I and its pharmaceutically acceptable salt, and its use in the preparation of drugs for the treatment of rheumatoid arthritis, wherein X is selected from oxygen, sulfur, —SO—, and —SO$_2$—; Y is a sulfur atom and Z is H, Na, or K. Through preliminary tests of anti-inflammatory activity, compounds of formula I have anti-rheumatoid arthritis effects.

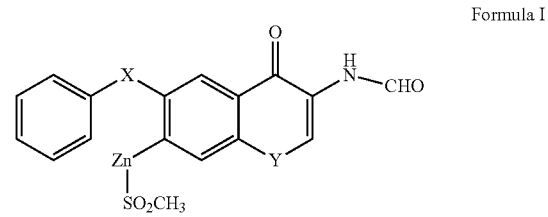

Formula I

6 Claims, 12 Drawing Sheets

THIOBENZOPYRANS AND THEIR USE IN PREPARATION OF DRUGS FOR TREATMENT OF RHEUMATOID ARTHRITIS

CROSS-REFERENCE TO RELATED APPLICATIONS

This application claims the priority to the Chinese application No. 2020107265649 filed with China National Intellectual Property Administration on Jul. 25, 2020, entitled "Thiobenzopyrans and their use in treatment of rheumatoid arthritis", the disclosure of which is incorporated by reference herein in its entirety.

TECHNICAL FIELD

The present disclosure relates to the field of medicinal chemistry, specifically to thiobenzopyrans having anti-inflammation activity and its use in the preparation of drugs for the treatment of rheumatoid arthritis.

BACKGROUND

Rheumatoid arthritis (RA) is a common systemic autoimmune disease, the basic lesion is chronic synovitis, abnormal synovium hyperplasia, thickening of the lining layer, cartilage formation from blood vessels, and bone tissue destruction, eventually leading to deformity and function loss of joints, serious impact on human health, and quality of life. In recent years, the incidence and prevalence of disability have been increasing year by year.

At present, for rheumatoid arthritis, there is no drug to cure it, and the drugs are used to merely delay the development of the disease. At present, the drugs currently used in clinical practice mainly include non-steroidal anti-inflammatory drugs, glucocorticoids, immunosuppressants, and interferons.

Iguratimod (T-614), a new non-steroidal anti-inflammatory drug for the treatment of rheumatoid arthritis, was jointly developed by Toyama and Eisai Pharmaceutical Co., Ltd., having a chemical name of 3-formamido-7-methylsulfonamido-6-phenoxy-4H-1-benzopyran-4-one. This drug can selectively inhibit cyclooxygenase COX-2, can regulate T cells and has autoimmune modulatory effects. It acts more rapidly compared with prior therapeutic drugs while having an efficacy equivalent to highly effective antirheumatic drugs and having a low toxicity. In addition, Iguratimod can also be administered orally.

As a relatively new type of non-steroidal anti-inflammatory drug, Iguratimod has the advantage of lower toxicity and minor side effects. However, long-term use of Iguratimod may still cause serious side effects such as significant increase in aminotransferases. Therefore, it is urgent to develop new drugs.

SUMMARY

To solve the problems existing in the prior art, the present disclosure provides thiobenzopyran-based compounds that can maintain the efficacy of Iguratimod while having lower toxicity and minor side effects.

The thiobenzopyran-based compound of the present disclosure has a structure shown in formula I:

Formula I wherein X is selected from O (oxygen), S (sulfur), —SO— (sulfenyl), —SO$_2$-(sulfonyl);
Y is S (sulfur); and Z is H, Na, or K.

In short, the compounds of the present disclosure include a series of derivatives having a basic structure of thiobenzopyranyl methanesulfonamide.

Specifically, the thiobenzopyran-based compounds of the present disclosure may be one of the following compounds:

Compound 1

Compound 2

Compound 3

Compound 4

Beneficial Effects of the Present Disclosure

In the present disclosure, the advantages and disadvantages of the structure of the thiobenzopyran-based compounds are analyzed by referring to the structural characteristics of Iguratimod. The moiety having anti-inflammatory activity in the structure is retained, and the compounds of the present disclosure are formed through a series of chemical reactions. The thiobenzopyran-based compounds of the present disclosure have a stronger anti-inflammatory effect following preliminary anti-inflammatory tests and have minor toxic side effects when compared with Iguratimod. Compared with Iguratimod, aminotransferase is not significantly elevated when the compounds of the present disclosure are consumed for a same period of time.

DETAILED DESCRIPTION OF THE EMBODIMENTS

Figure 1:
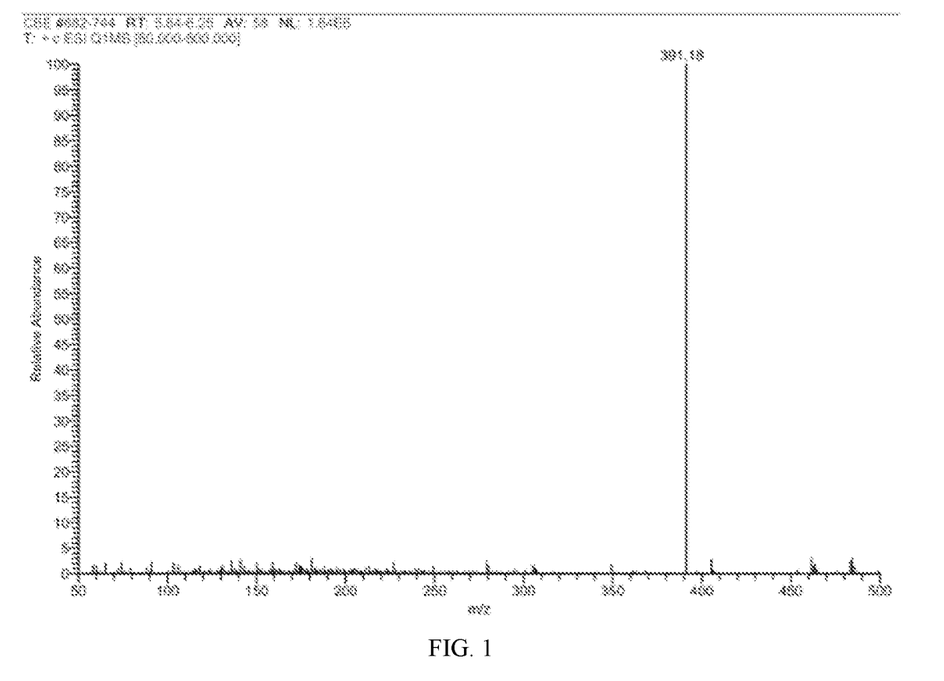
FIG. 1 is a mass spectrum of compound 1 of the present disclosure.
Figure 2:
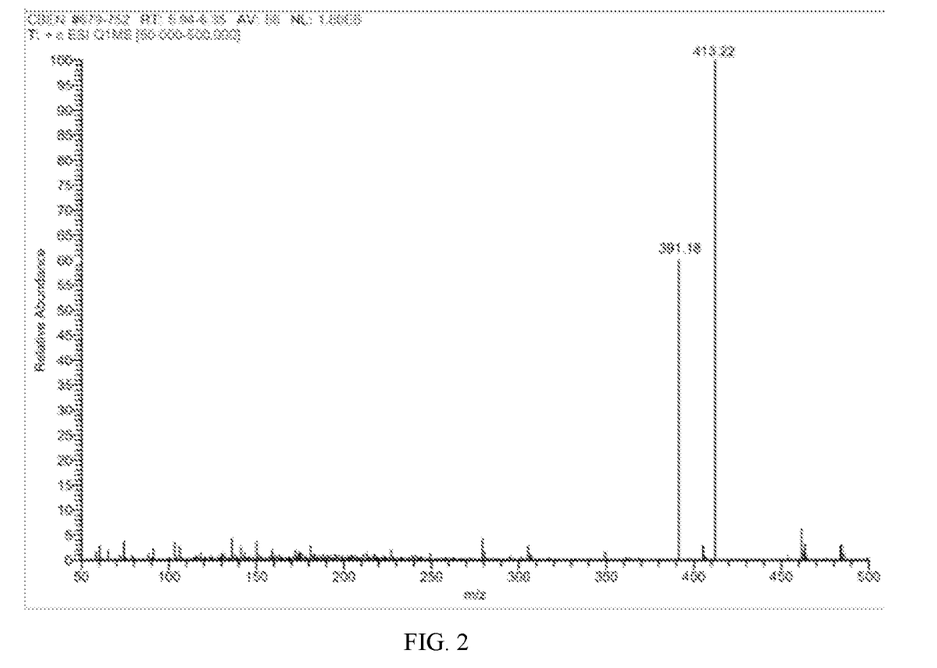
FIG. 2 is a mass spectrum of the sodium salt of compound 1 of the present disclosure.
Figure 3:
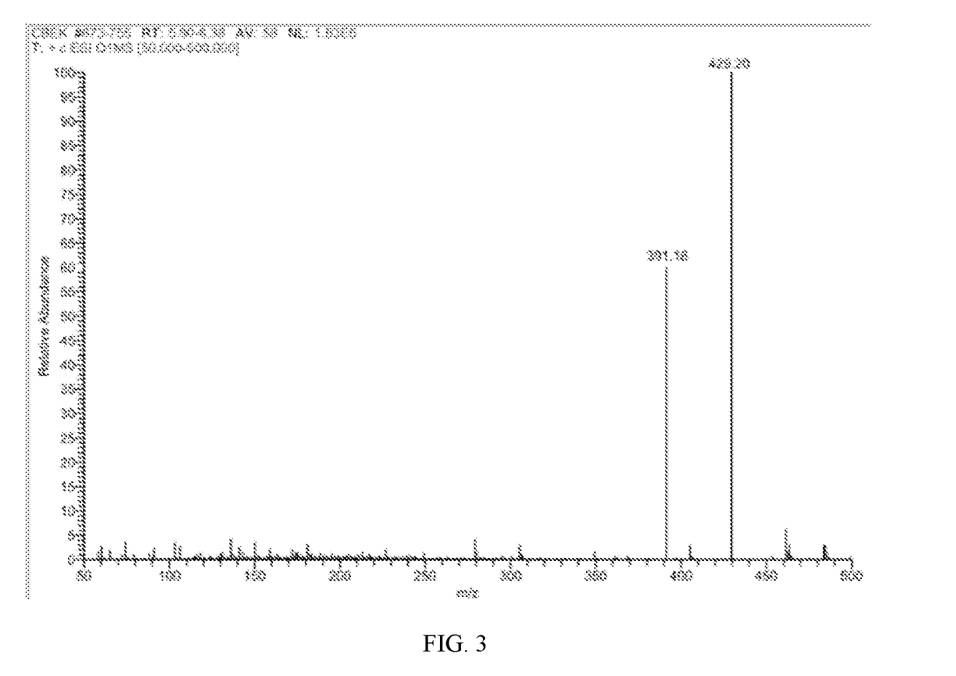
FIG. 3 is a mass spectrum of the potassium salt of compound 1 of the present disclosure.
Figure 4:
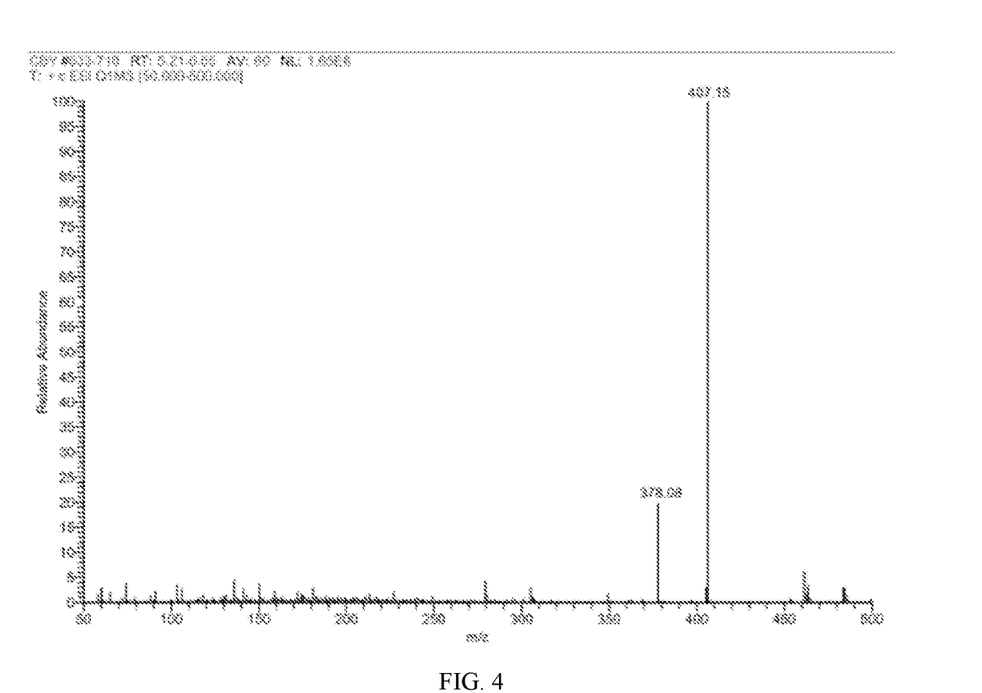
FIG. 4 is a mass spectrum of compound 2 of the present disclosure.
Figure 5:
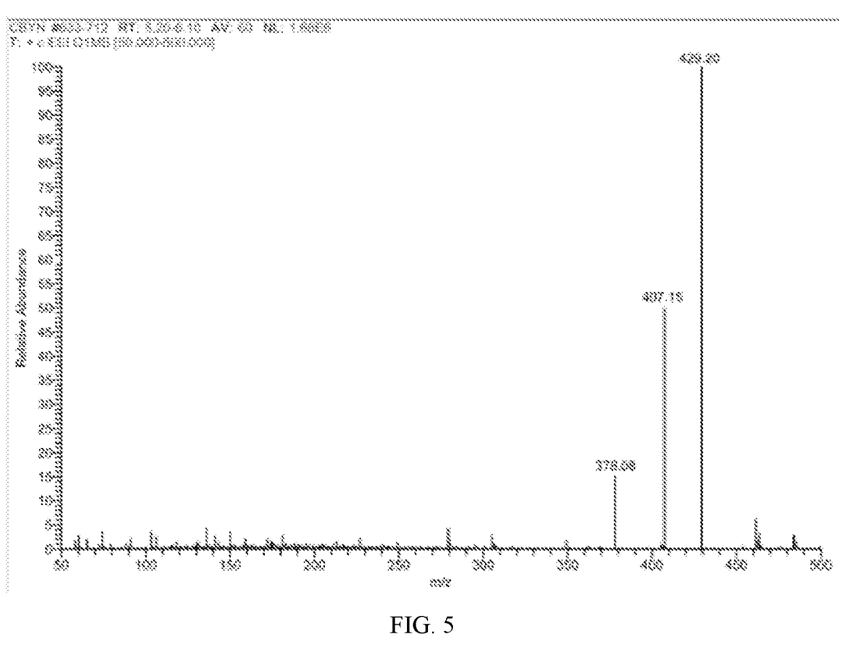
FIG. 5 is a mass spectrum of the sodium salt of compound 2 of the present disclosure.
Figure 6:
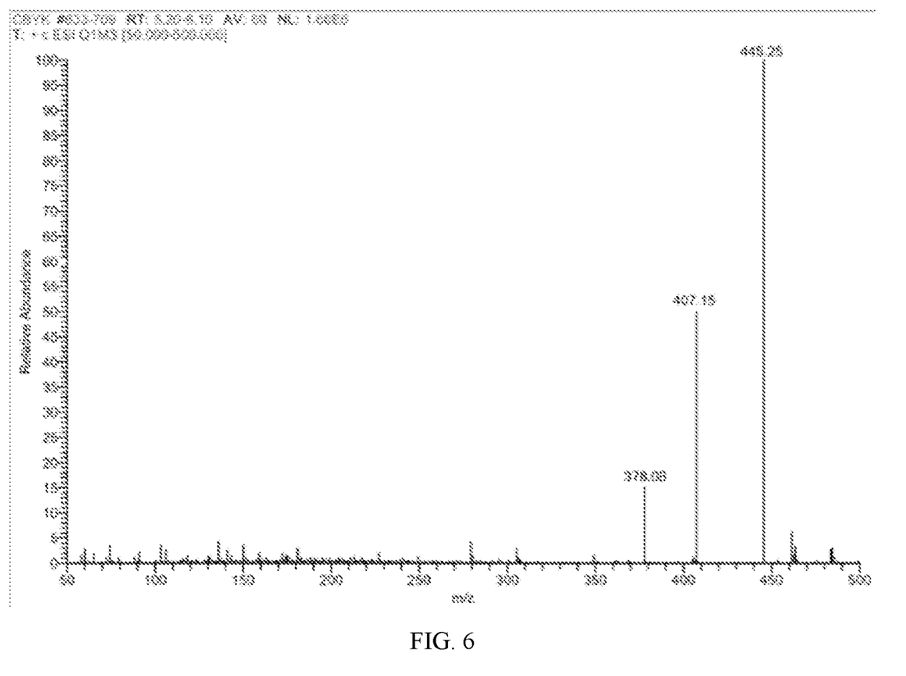
FIG. 6 is a mass spectrum of the potassium salt of compound 2 of the present disclosure.
Figure 7:
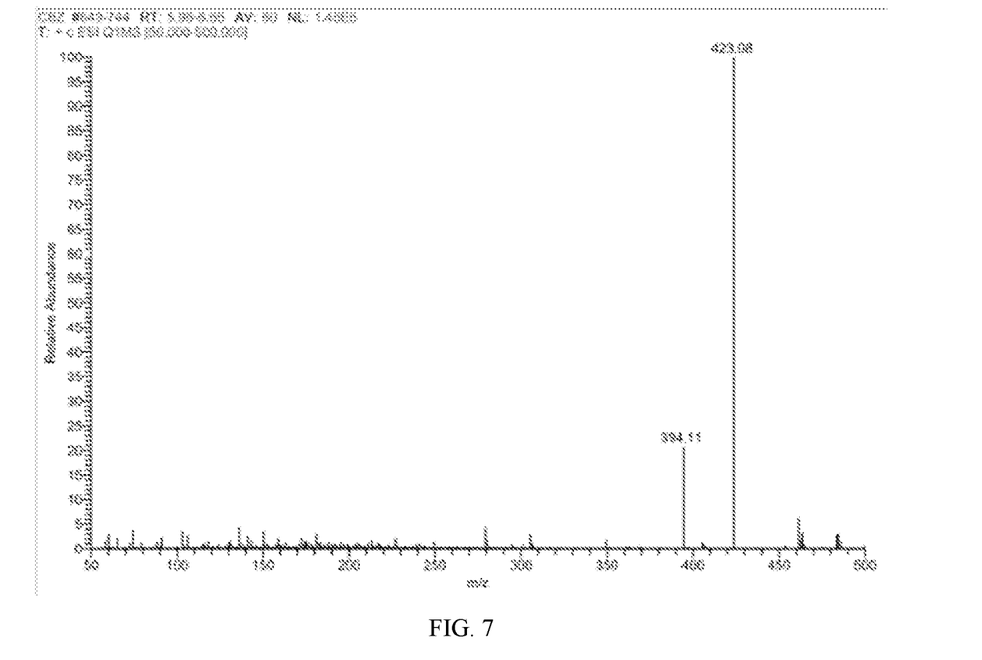
FIG. 7 is a mass spectrum of compound 3 of the present disclosure.
Figure 8:
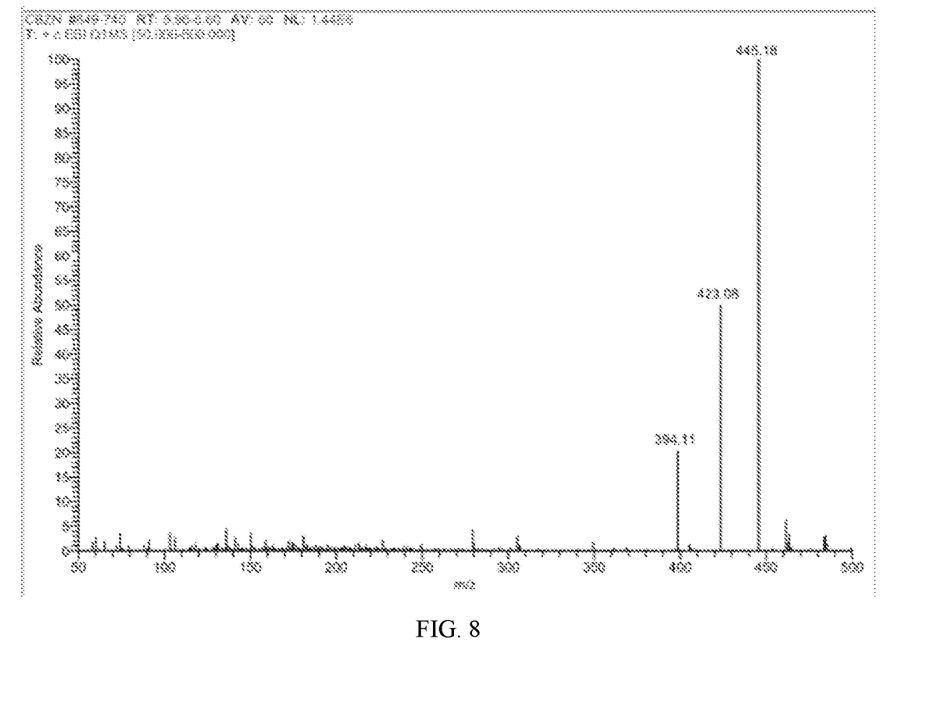
FIG. 8 is a mass spectrum of the sodium salt of compound 3 of the present disclosure.
Figure 9:
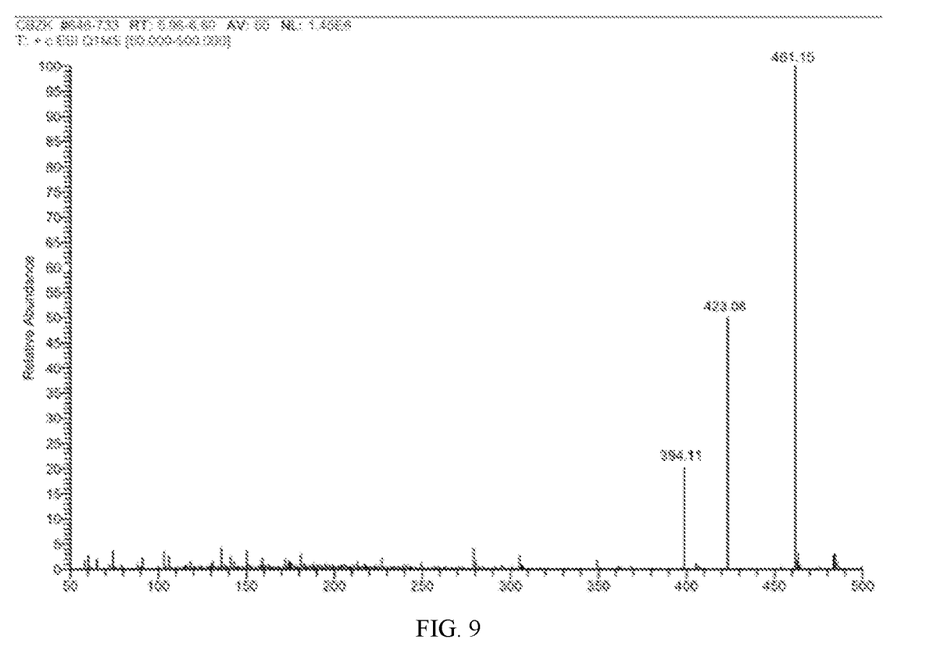
FIG. 9 is the mass spectrum of the potassium salt of compound 3.
Figure 10:
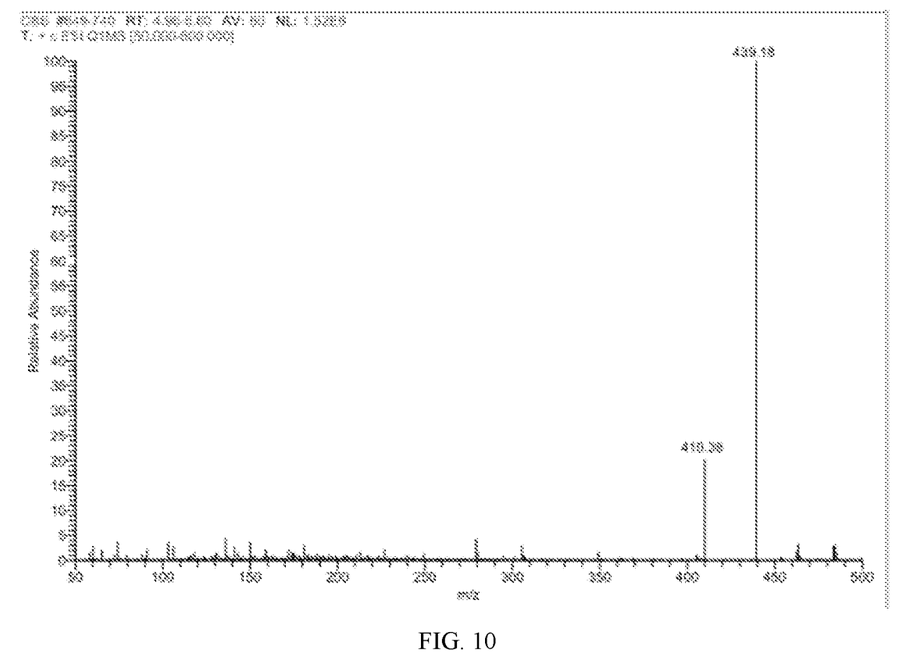
FIG. 10 is a mass spectrum of compound 4 of the present disclosure.
Figure 11:
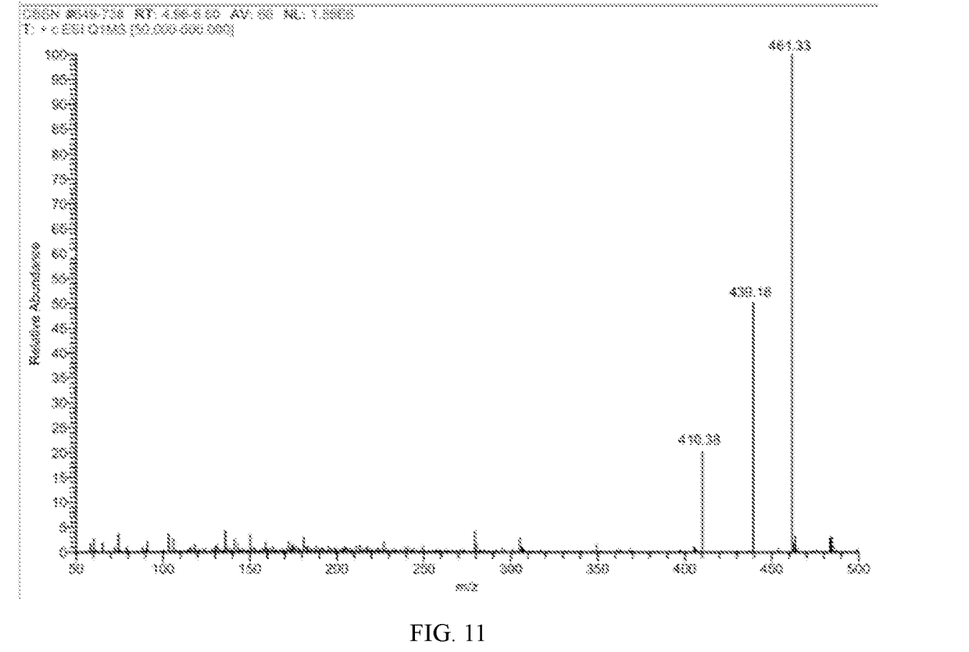
FIG. 11 is a mass spectrum of the sodium salt of compound 4 of the present disclosure.
Figure 12:
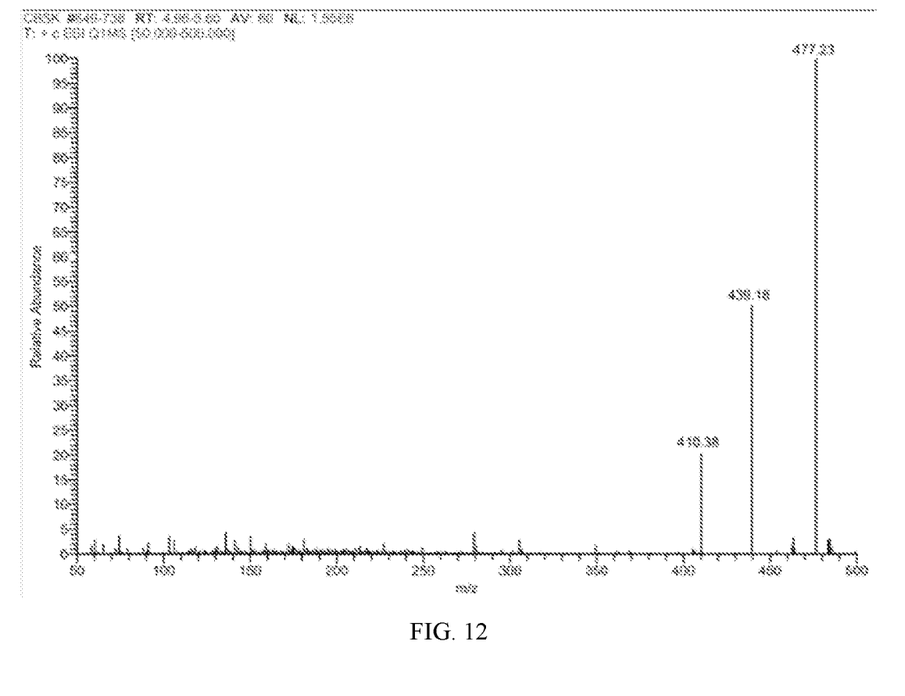
FIG. 12 is a mass spectrum of the potassium salt of compound 4 of the present disclosure.

To better illustrate the spirit of the present disclosure and implement the present disclosure, the following embodiments are provided. Those skilled in the art should be aware that embodiments are merely intended to demonstrate the process of the present disclosure and do not affect the scope of the present disclosure.

During the preparation of the compounds of the present disclosure, common chemical raw materials in the market are chosen. The target compounds are obtained after a series of reaction steps. For some reaction steps, reference can be made to U.S. Pat. No. 4,411,910, in which a method for preparing Iguratimod is described. The method can be expressed by the scheme as follows:

wherein X is O or S.

Example 1

Synthesis of 3-nitro-4-phenoxythioanisole

Phenol (32.9 g) and 4-chloro-3-nitrothioanisole (50 g) were added to 100 ml of DMF, after the resulting mixture was stirred well, potassium t-butoxide (47.5 g) was added and the resulting mixture was heated at 110° C. for 4 hours. The reaction mixture was poured into 200 ml of icy water, extracted with 3*300 ml of ethyl acetate, and the organic phase was washed with 100 ml of 1 M hydrochloric acid and water. The organic phase was dried over anhydrous magnesium sulfate and concentrated to dryness. Dichloromethane was added to the residue for crystallization to afford 3-nitro-4-phenoxythioanisole.

Example 2

Synthesis of 3-amino-4-phenoxythioanisole 3-nitro-4-phenoxythioanisole (45 g) was dissolved in 500 ml of absolute ethanol, and the hydrogenation reaction was carried out at room temperature for 3 hours under conditions of 10 wt % palladium carbon at 0.3 MPa of hydrogen pressure. The reaction mixture was filtered, and the filtrate was concentrated under reduced pressure to yield the reduction product. The reduction product was recrystallized in toluene to afford 3-amino-4-phenoxythioanisole.

Example 3

Synthesis of 3-methylsulfonamido-4-phenoxythioanisole 3-amino-4-phenoxythioanisole (30 g) was dissolved in pyridine (150 ml) and methanesulfonyl chloride (18 g) was added at a temperature of 0-5° C., AFTER the addition, the resulting mixture was stirred at room temperature for 1 hour. The reactants were poured into 200 ml of icy water, extracted s with 3*300 ml of ethyl acetate, and the organic phase was washed with 100 ml of 1M diluted hydrochloric acid solution and water. The organic phase was dried over anhydrous magnesium sulfate and concentrated to dryness. The residue was recrystallized in ethanol to give 3-methylsulfonamido-4-phenoxythioanisole.

Example 4

Synthesis of α-amino-2-methylthio-4-methylsulfonamido-5-phenoxyacetophenone hydrochloride Aluminum chloride (54 g) and aminoacetonitrile hydrochloride (18.5 g) were added to 200 ml of nitrobenzene under stirring in batches at room temperature and cooled to 10° C., 3-methylsulfonamido-4-phenoxythioanisole was added, then hydrogen chloride gas was introduced, and the reaction mixture was stirred for 10 hours at 25-30° C. The reactants were poured into 500 ml of cold diluted hydrochloric acid (3M), and precipitates appeared. The precipitates were filtered, washed with ethyl acetate, and dried to afford α-amino-2-methylthio-4-methylsulfonamido-5-phenoxyacetophenone hydrochloride.

Example 5

Preparation of α-formamido-2-methylthio-4-methylsulfonamido-5-phenoxyacetophenone Valeryl chloride (15 g) was dissolved in 100 ml of acetone, sodium formate monohydrate (17 g) was added and stirred vigorously for 4 h at room temperature, and then α-amino-2-methylthio-4-methylsulfonamido-5-phenoxyacetophenone hydrochloride (33 g) was added. The resulting mixture was stirred for further 5 hours. Then 300 ml of water was added and precipitates occurred. The precipitates were filtered, washed with water and isopropyl alcohol, and dried to give a crude product. The crude product was recrystallized in acetonitrile to afford pure α-formamido-2-methylthio-4-methylsulfonamido-5-phenoxyacetophenone.

Example 6

Preparation of α-formamido-2-mercapto-4-methylsulfonamido-5-phenoxyacetophenone

In an ice/water bath, the temperature was controlled below 20° C., and aluminum chloride (23 g) was added to 100 ml of acetonitrile, and then sodium iodide (12.8 g), α-formamido-2-methylthio-4-methylsulfonamido-5-phenoxyacetophenone (26 g) were added and stirred for 6 hours at 20° C. The reactants were poured into 350 ml of 1 wt % sodium sulfite aqueous solution to produce yellow-white precipitates. The precipitates were filtered, washed with 250 ml of water and 200 ml of ethanol, and dried to give a crude product. The crude product was recrystallized in acetonitrile, and a pure product α-formamido-2-mercapto-4-methylsulfonamido-5-phenoxyacetophenone was obtained.

Example 7

Synthesis of target product 3-formamido-7-methylsulfonamido-6-phe noxy-4H-I-thiobenzopyran-4-one (i.e. compound 1)

Alpha-formamido-2-mercapto-4-methylsulfonamido-5-phenoxyacetophenone (20 g) was dissolved in 100 ml of dichloromethane at 10° C., and then N,N-dimethylformamide dimethyl acetal (20 g) was added, and 10 ml of triethylamine was added. The resulting mixture was stirred at 20° C. for 6 hours, and then 150 ml of water was added. The reaction mixture was filtered, and the filter cake was washed with dichloromethane, water, and ethanol and dried to give a crude product. The crude product was recrystallized in acetonitrile to give the target compound, named compound 1. The mass-to-charge ratio $[M+H]^+$ of the target compound ion was 391.18, which was consistent with the molecular weight of the target compound (390.03).

Example 8

Synthesis of 3-nitro-4-(phenylthio)thioanisole

Thiophenol (32.9 g) and 4-chloro-3-nitrothioanisole (50 g) were added to DMF (100 ml). After stirring well, potassium t-butoxide (47.5 g) was added and the resulting mixture was heated at 110° C. for 4 hours. The reaction mixture was poured into 200 ml of icy water extracted with 3*300 ml of ethyl acetate, and the organic phase was washed with 100 ml of 1M hydrochloric acid and then with water. The organic phase was dried over anhydrous magnesium sulfate and concentrated to dryness. Dichloromethane was added to the residue for crystallization, and 3-nitro-4-(phenylthio)thioanisole was obtained.

Example 9

Synthesis of 3-amino-4-(phenylthio)thioanisole 3-nitro-4-(phenylthio)thioanisole (45 g) was dissolved in 500 ml of absolute ethanol, hydrogenation reaction was carried out at room temperature for 3 hours under the conditions of 10 wt % palladium carbon and 0.3 MPa hydrogen pressure. The reaction mixture was filtered, the reduction product was obtained by concentration under reduced pressure, and the residue was recrystallized in toluene to give 3-amino-4-phenoxythioanisole.

Example 10

Synthesis of 3-methylsulfonamido-4-(phenylthio)thioanisole 3-amino-4-(phenylthio)thioanisole (30 g) was dissolved in 150 ml of pyridine, 18 g of methanesulfonyl chloride was added at a temperature of 0-5° C., and the resulting mixture was stirred for 1 hour at room temperature after addition. The reactants were poured into 200 ml of icy water and extracted with 3*300 ml of ethyl acetate. The organic phase was washed with 1M diluted hydrochloric acid (100 ml), washed with water, and the organic phase was dried over anhydrous magnesium sulfate and concentrated to dryness. The residue was recrystallized in ethanol to give 3-methylsulfonamido-4-(phenylthio)thioanisole.

Example 11

Synthesis of α-amino-2-methylthio-4-methylsulfonamido-5-phenylthioacetophenone hydrochloride Aluminum chloride (54 g) and aminoacetonitrile hydrochloride (18.5 g) were added to 200 ml of stirred nitrobenzene in batches at room temperature and cooled to 10° C., 3-methylsulfonamido-4-(phenylthio)thioanisole was added, hydrogen chloride gas was introduced and the resulting mixture was stirred at 25-30° C. for 10 hours. The reactants were poured into 500 ml of cold diluted hydrochloric acid (3M) and precipitates appeared. The precipitates were filtered, washed with ethyl acetate, and dried to give α-amino-2-methylthio-4-methylsulfonamido-5-phenylthioacetophenone hydrochloride.

Example 12

Preparation of α-formamido-2-methylthio-4-methylsulfonamido-5-phenylthioacetophenone Valeryl chloride (15 g) was dissolved in 100 ml of acetone, sodium formate monohydrate (17 g) was added and the resulting mixture was stirred vigorously for 4 h at room temperature, and then α-amino-2-methylthio-4-methylsulfonamido-5-phenylthioacetophenone hydrochloride (33 g) was added and stirred for further 5 hours. 300 ml of water was added, and precipitates occurred. The precipitates were filtered, washed with water and isopropyl alcohol, and dried to give a crude product. The crude product was recrystallized in acetonitrile to afford pure α-formamido-2-methylthio-4-methylsulfonamido-5-phenylthioacetophenone.

Example 13

Preparation of α-formamido-2-mercapto-4-methylsulfonamido-5-phenylthioacetophenone In an ice/water bath, the temperature was controlled below 20° C., aluminum chloride (23 g) was added to 100 ml of acetonitrile, and then sodium iodide (12.8 g), α-formamido-2-methylthio-4-methylsulfonamido-5-phenylthioacetophenone (26 g) were added and the resulting mixture was stirred at 20° C. for 6 hours. The reactants were poured into 350 ml of 1% sodium sulfite aqueous solution. Yellow-white precipitates were precipitated, and the precipitates were filtered, washed with 250 ml of water and 200 ml of ethanol, and dried to give a crude product. The crude product was recrystallized in acetonitrile to give pure α-formamido-2-mercapto-4-methylsulfonamido-5-phenylthioacetophenone.

Example 14

Synthesis of target product 3-formamido-7-methylsulfonamido-6-phenylthio-4H-1-thiobenzopyran-4-one (i.e. compound 2)

Alpha-formamido-2-mercapto-4-methylsulfonamido-5-phenylthioacetophenone (20 g) was dissolved in 100 ml of dichloromethane at 10° C., and then N,N-dimethylformamide dimethyl acetal (20 g) was added, 10 ml of triethylamine was added. The resulting mixture was stirred at 20° C. for 6 hours. Then 150 ml of water was added and the reaction mixture was filtered. The filter cake was washed with dichloromethane, water, and ethanol, and dried to give a crude product. The crude product was recrystallized in acetonitrile to give the target compound, namely compound 2. The mass-to-charge ratio [M+H]$^+$ of the target compound ion was 407.15, which was consistent with the molecular weight of the target compound (406.01).

Example 15

Synthesis of target product N-(7-(methylsulfonamido)-4-oxo-6-(phenylsulfenyl)-4H-thiobenzopyran-3-yl)carboxamide (i.e. compound 3)

Compound 2 (15 g) was mixed with water evenly, 30 wt % hydrogen peroxide (4.1 g) was added dropwise at room temperature, and the reaction mixture was stirred at room temperature and allowed to react for 10 hours until the raw materials were completely consumed. The reaction mixture was filtered and washed with water. The reaction products were separated by column chromatography to give the target compound, which was named compound 3. The mass-to-charge ratio [M+H]$^+$ of the target compound ion was 423.08, which was consistent with the molecular weight of the target compound (422.01).

Example 16

Synthesis of target product N-(7-(methylsulfonamido)-4-oxo-6-(phenylsulfonyl)-4H-thiobenzopyran-3-yl)carboxamide (i.e. compound 4)

Compound 2 (15 g) was mixed with water evenly, 30 wt % hydrogen peroxide (6.5 g) was added dropwise at room temperature, and the reaction mixture was stirred at room temperature and allowed to react for 10 hours until the raw materials were completely consumed. The reaction mixture was filtered and washed with water. The reaction products were separated by column chromatography to give target compound 4. The mass-to-charge ratio [M+H]$^+$ of the target compound ion was 439.18, which was consistent with the molecular weight of the target compound (438.00).

Example 17

Preparation of Sodium Salts of Compound 1

Compound 1 (1 g) was placed in a flask, and 200 ml of absolute ethanol was added, heated reflux to dissolve the solids. Then 182 mg of sodium ethoxide was added dropwise and the mixture was stirred for 2 hours. Then 0.3 g of activated carbon was added and stirred for another 30 minutes, and the reaction mixture was filtered. Two-thirds of the solvent in the filtrate was removed by evaporation, the remaining solvent was cooled and subject to crystallization. Filtration was conducted and the solids were rinsed with a small amount of absolute ethanol and dried, and sodium salt of compound 1 was thus obtained.

Sodium salts of compound 2, compound 3, and compound 4 were synthesized using the same method.

Example 18

Preparation of Potassium Salts of Compound 1

Compound 1 (1 g) was added to 200 ml of absolute ethanol, heated to reflux to dissolve the solids, then potassium ethanol (187 mg) was added dropwise. The resulting mixture was stirred for 2 hours, and then 0.3 g of activated carbon was added and stirred for 30 minutes. The reaction mixture was filtered and two-thirds of the solvent in the filtrate was removed by evaporation, and the remaining solvent was cooled and was subject to crystallization, and filtration was performed. The solids were washed with a small amount of absolute ethanol and dried to give potassium salt of compound 1.

Potassium salts of Compound 2, Compound 3, and Compound 4 were synthesized using the same method.

Example 19

Preparation of Hard Capsules Containing Compound 1

TABLE 1

| Formulation for hard capsules containing compound 1 | |
| --- | --- |
| Compound 1 | 50 mg |
| Lactose | 114 mg |
| Corn starch | 20 mg |
| Hydroxypropancellulose | 2 mg |
| Silicon dioxide | 2 mg |
| Calcium carboxymethylcellulose | 10 mg |
| Magnesium stearate | 2 mg |
| Total | 200 mg |

The above components were packed into hard capsules according to a conventional method.

Hard capsules of sodium salt and potassium salt of compound 1, hard capsules of compound 2 and its sodium salt and potassium salt, hard capsules of compound 3 and its sodium salt and potassium salt, and hard capsules of compound 4 and its sodium salt and potassium salt were prepared using the same method.

Example 20

Preparation of Tablets Containing Compound 2

TABLE 2

| Formulation for tablets containing compound 2 | |
| --- | --- |
| Compound 2 | 25 mg |
| Lactose | 50 mg |
| Microcrystalline cellulose | 26 mg |
| Hydroxypropancellulose | 2 mg |
| Carboxymethylcellulose | 6.6 mg |
| Magnesium stearate | 1.2 mg |
| Talcum powder | 1.2 mg |
| Total | 100 mg |

The above components were compressed into tablets according to conventional methods.

Tablets of compound 1, its potassium salt and its sodium salt, tablets of potassium salt and sodium salt of compound 2, tablets of compound 3, its potassium and its sodium salt, and tablets of compound 4, its potassium salt and sodium salt were prepared using the same method.

Test Example 1

The study on the anti-arthritic activity of the compounds of the present disclosure was conducted based on the animal model of adjuvant arthritis (AA) of rats and on the establishment of adjuvant arthritis of rats. The rats were divided into 14 groups, with 10 rats in each group, and the rats were administered by gavage the compound of the present disclosure, a blank control, and a positive control substance of Iguratimod at a dose of 50 μg/dose/day for consecutive 5 days. A drainage method was used to determine the degree of foot swelling in rats of each group before and after administration, and the degree of foot swelling in rats before and after administration was calculated to determine whether the drug was effective.

Foot swelling degree X=(volume of the toe after inflammation−volume of toe before inflammation)/volume of the toe before inflammation×100%. The test results are shown in Table 3 below.

TABLE 3

| Group | Number of cases | The average swelling degree before administration($\bar{X} \pm s$) | Average swelling degree after administration($\bar{X} \pm s$) |
| --- | --- | --- | --- |
| Blank control group | 10 | 0.438 ± 0.0291 | 0.425 ± 0.0305 |
| Iguratimod group | 10 | 0.445 ± 0.0321 | 0.029 ± 0.0389 |
| Compound 1 group | 10 | 0.453 ± 0.0290 | 0.020 ± 0.0335 |
| Compound 1 sodium salt group | 10 | 0.450 ± 0.0284 | 0.023 ± 0.0306 |
| Compound 1 potassium salt group | 10 | 0.455 ± 0.0279 | 0.020 ± 0.0323 |
| Compound 2 group | 10 | 0.430 ± 0.0312 | 0.019 ± 0.0315 |
| Compound 2 sodium salt group | 10 | 0.448 ± 0.0291 | 0.020 ± 0.0325 |
| Compound 2 potassium salt group | 10 | 0.453 ± 0.0290 | 0.021 ± 0.0335 |
| Compound 3 group | 10 | 0.449 ± 0.0305 | 0.025 ± 0.0339 |
| Compound 3 sodium salt group | 10 | 0.438 ± 0.0229 | 0.022 ± 0.0333 |
| Compound 3 potassium salt group | 10 | 0.454 ± 0.0277 | 0.023 ± 0.0330 |
| Compound 4 group | 10 | 0.425 ± 0.0247 | 0.017 ± 0.0305 |
| Compound 4 sodium salt group | 10 | 0.435 ± 0.0290 | 0.018 ± 0.0303 |
| Compound 4 potassium salt group | 10 | 0.418 ± 0.0198 | 0.019 ± 0.0274 |

The test results proved that the anti-inflammatory effect of the compounds of the present disclosure was better than that of Iguratimod, wherein compound 4 and its salts had a better anti-inflammatory effect.

Test Example 2

Elevated aminotransferase is a common side effect of Iguratimod. To investigate whether the compounds of the present disclosure have effects on aminotransferase, healthy rats were administered orally the compound of the present disclosure and Iguratimod for 15 days, respectively, and then the content of aminotransferase in the serum of rats was determined. The test results are shown in Table 4 below.

TABLE 4

| Group | Number of cases | ALT (U/L) | AST(U/L) |
| --- | --- | --- | --- |
| Blank control group | 10 | 31.52 ± 4.58 | 35.80 ± 5.44 |
| Iguratimod group | 10 | 173 ± 9.86 | 145 ± 10.98 |
| Compound 1 group | 10 | 125 ± 10.24 | 75 ± 8.22 |
| Compound 1 sodium salt group | 10 | 129 ± 10.18 | 76 ± 9.22 |
| Compound 1 potassium salt group | 10 | 126 ± 10.05 | 78 ± 8.74 |
| Compound 2 group | 10 | 108 ± 9.43 | 80 ± 9.28 |
| Compound 2 sodium salt group | 10 | 104 ± 9.05 | 76 ± 9.56 |
| Compound 2 potassium salt group | 10 | 109 ± 9.11 | 77 ± 9.02 |
| Compound 3 group | 10 | 143 ± 7.83 | 90 ± 8.76 |
| Compound 3 sodium salt group | 10 | 140 ± 8.83 | 87 ± 9.06 |
| Compound 3 potassium salt group | 10 | 141 ± 7.89 | 89 ± 8.91 |
| Compound 4 group | 10 | 133 ± 9.04 | 79 ± 9.82 |
| Compound 4 sodium salt group | 10 | 130 ± 9.15 | 83 ± 8.09 |
| Compound 4 potassium salt group | 10 | 132 ± 8.79 | 85 ± 6.87 |

It can be seen from the above results that the side effects produced by orally taking the compounds of the present disclosure are significantly weaker than that of Iguratimod, wherein compound 2 and its salts have further weaker side effects.

What is claimed is:

1. A thiobenzopyran-based compound of Formula I or their pharmaceutically acceptable salts,

Formula I wherein X was selected from —SO—, and —SO$_2$—;
Y is a sulfur atom; and
Z is H, Na, or K.

2. The thiobenzopyran-based compound or pharmaceutically acceptable salts according to claim 1, wherein the thiobenzopyran-based compound is selected from one of the following compounds:

Compound 3

Compound 4

3. A pharmaceutical composition, wherein the pharmaceutical composition comprises the thiobenzopyran-based compound or pharmaceutically acceptable salts thereof according to claim 1.

4. A method for treating rheumatoid arthritis, comprising a step of administering the thiobenzopyran-based compound or pharmaceutically acceptable salts according to claim 1 to a patient in need thereof.

5. A method for treating rheumatoid arthritis, comprising a step of administering the thiobenzopyran-based compound or pharmaceutically acceptable salts according to claim 2 to a patient in need thereof.

6. A pharmaceutical composition, wherein the pharmaceutical composition comprises the thiobenzopyran-based compound or pharmaceutically acceptable salts thereof according to claim 2.

* * * * *